(12) United States Patent
Naidu

(10) Patent No.: US 7,585,986 B2
(45) Date of Patent: Sep. 8, 2009

(54) SEMI-SYNTHESIS OF TAXANE INTERMEDIATES AND AZIRIDINE ANALOGUES AND THEIR CONVERSION TO PACLITAXEL AND DOCETAXEL

(75) Inventor: Ragina Naidu, Burnaby (CA)

(73) Assignee: Chatham Biotec, Limited, Riverview, New Brunswick (CA)

( * ) Notice: Subject to any disclaimer, the term of this patent is extended or adjusted under 35 U.S.C. 154(b) by 0 days.

(21) Appl. No.: 10/590,647

(22) PCT Filed: Feb. 24, 2005

(86) PCT No.: PCT/US2005/005953

§ 371 (c)(1),
(2), (4) Date: Jul. 20, 2007

(87) PCT Pub. No.: WO2005/082875

PCT Pub. Date: Sep. 9, 2005

(65) Prior Publication Data

US 2008/0033189 A1    Feb. 7, 2008

(51) Int. Cl.
*C07D 305/00*    (2006.01)
*C07D 405/00*    (2006.01)
(52) U.S. Cl. .................. 549/510; 549/511; 548/964
(58) Field of Classification Search ............. 549/510, 549/511; 548/964
See application file for complete search history.

(56) References Cited

U.S. PATENT DOCUMENTS

| 5,319,112 A | 6/1994 | Kingston et al. |
| 5,808,113 A | 9/1998 | Murray et al. |
| 7,202,370 B2 * | 4/2007 | Naidu .................. 549/510 |

OTHER PUBLICATIONS

Gennari et al. "Rational designed chiral enaol borinates . . ." Pure & Appl. Chem. vol. 69(3) (1997) p. 507-512.*
Gennari et al. "Computer assisted design and synthesis . . ." J. Braz. chem. soc. vol. 9(4)(1998) p. 319-326.*
Chen et al. "Synthesis and biological evaluation . . ." CA 123:112445 (1995).*
Beckvermit et al., "An Improved Method for Separating Paclitaxel and Cephalomannine Using Ozone and Girard Reagents," *J. Org. Chem.* 61(25):9038-9040, 1996.
Commercon et al., "Improved Protection and Esterification of a Precursor of the TAXOTERE® and Taxol Side Chains," *Tetrahedron Letters* 33(36):5185-5188, 1992.
Pines et al., "The Stereochemistry of 2,3-Diphenyl-1-methylpropylamine," *Journal of Medical Chemistry* 10(4):725-728, 1967.
Rimoldi et al., "An Improved Method for the Separation of Paclitaxel and Cephalomannine," *Journal of Natural Products* 59(2):167-168, 1996.

* cited by examiner

*Primary Examiner*—Janet L. Andres
*Assistant Examiner*—Raymond Covington
(74) *Attorney, Agent, or Firm*—Klarquist Sparkman, LLP

(57) ABSTRACT

A process is provided for the semi-synthesis of taxane intermediates and aziridine analogues of cephalomannine and baccatin III intermediates, and the conversion of such intermediates and analogues to paclitaxel and docetaxel.

18 Claims, 7 Drawing Sheets

SEMI-SYNTHESIS OF TAXANE INTERMEDIATES AND AZIRIDINE ANALOGUES AND THEIR CONVERSION TO PACLITAXEL AND DOCETAXEL

CROSS REFERENCE TO RELATED APPLICATIONS

This application is the U.S. National Stage of International Application No. PCT/US2005/005953, filed Feb. 24, 2005, which was published in English under PCT Article 21(2), which claims the benefit of the earlier filing dates of U.S. application Ser. No. 10/785,422, filed Feb. 24, 2004, and U.S. application Ser. No. 10/790,622, filed Mar. 1, 2004.

BACKGROUND OF THE INVENTION

1. Field of the Invention

The present invention relates to the semi-synthesis of taxane intermediates and aziridine analogues, in particular, aziridine analogues of cephalomannine and baccatin III intermediates, and their conversion to active antitumor agents, paclitaxel and docetaxel.

2. Description of the Prior Art

Docetaxel (1, Taxotere), a semi-synthetic analog, and paclitaxel (2, Taxol), a complex diterpene isolated from the bark of the Pacific yew tree (*Taxus brevifolia*) are arguably the most outstanding cancer chemotherapeutic substances discovered in recent times. While paclitaxel can be obtained from the yew tree or semi-synthetically, only the latter option is currently available for the formation of non-natural docetaxel. The partial synthesis of this important compound has generally been accomplished through esterification of a derivative of the (2R, 3S) phenylisoserine side chain with a protected form of 10-deacetylbaccatin III, a comparatively abundant natural product also present in the yew tree.

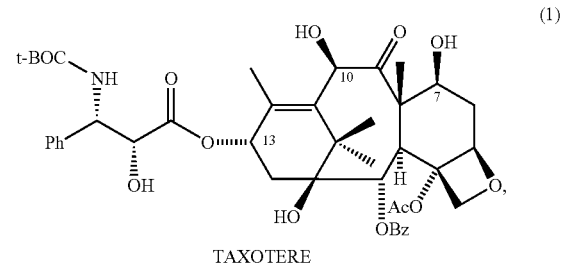

TAXOTERE (1)

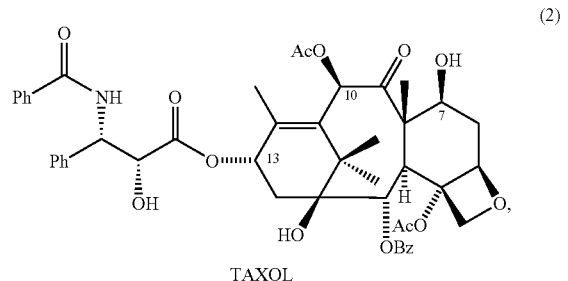

TAXOL (2)

In Colin's U.S. Pat. No. 4,814,470, it was reported that docetaxel has an activity significantly greater than paclitaxel.

Docetaxel and paclitaxel may be prepared semi-synthetically from 10-deacetylbaccatin III or baccatin III as set forth in U.S. Pat. Nos. 4,924,011 and 4,924,012 or by the reaction of a β-lactam and a suitably protected 10-deacetylbaccatin III or baccatin III derivative as set forth in U.S. Pat. No. 5,175,315. 10-deacetylbaccatin III (10-DAB, 3) and Baccatin III (4) can be separated from mixtures extracted from natural sources such as the needles, stems, bark or heartwood of numerous *Taxus* species and have the following structures.

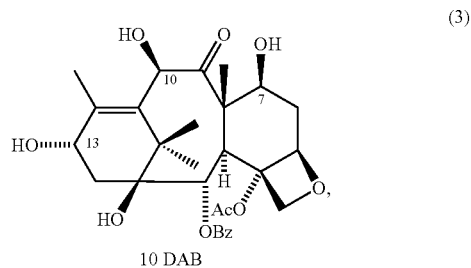

10 DAB (3)

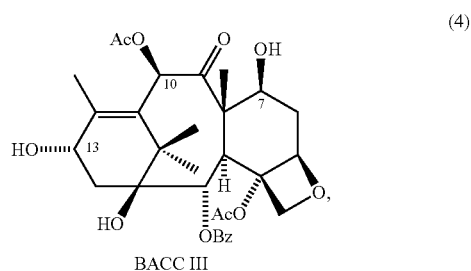

BACC III (4)

Although, most of the research towards the semi-synthesis of docetaxel and paclitaxel has involved 10-deacetylbaccatin III as the starting material, other taxanes present in the yew tree, such as 9-dihydro-13-acetylbaccatin III (9DHB, 5), present in the Canadian yew (*Taxus Canadensis*), and cephalomannine (6) have been collected and identified.

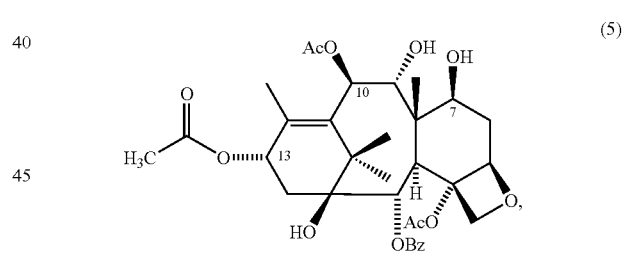

9DHB (5)

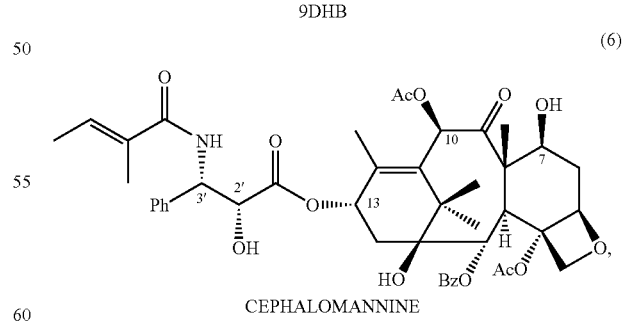

CEPHALOMANNINE (6)

As disclosed in U.S. patent application Ser. No. 10/695,416, which application is assigned to the assignee of the present invention, docetaxel and pacliaxel may also be prepared semi-synthetically from 9-dihydro-13-acetylbaccatin III.

Although there have been many advances in the field, there remains a need for new and improved processes for the preparation of taxane intermediates and their conversion to docetaxel and paclitaxel. The present invention addresses these needs and provides further related advantages.

BRIEF SUMMARY OF THE INVENTION

In brief, the present invention relates to the semi-synthesis of novel taxane intermediates and aziridine analogues, in particular, aziridine analogues of cephalomannine and baccatin III intermediates, and their conversion to active antitumor agents, paclitaxel and docetaxel.

In a first embodiment, the present invention provides a process for preparing a taxane comprising the steps of (1) converting cephalomannine to a taxane intermediate having the structure:

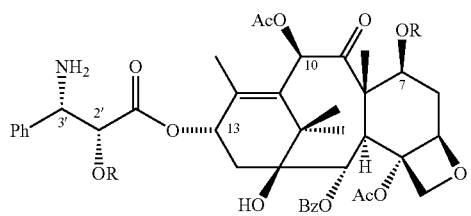

wherein R is at each occurrence independently selected from hydrogen and a hydroxy-protecting group, and (2) converting the taxane intermediate to paclitaxel or docetaxel.

In a more specific embodiment of the foregoing process, the step of converting cephalomannine to the taxane intermediate further comprises the steps of (1) converting cephalomannine to a cephalomannine aziridine analogue having the structure:

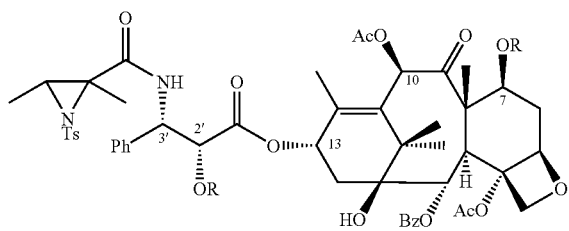

wherein R is at each occurrence independently selected from hydrogen and a hydroxy-protecting group, and (2) converting the cephalomannine aziridine analogue to the taxane intermediate.

In an alternate more specific embodiment of the foregoing process, the step of converting cephalomannine to the taxane intermediate comprises reacting cephalomannine with formic acid.

In yet another alternate more specific embodiment, the step of converting cephalomannine to the taxane intermediate further comprises the reaction sequence:

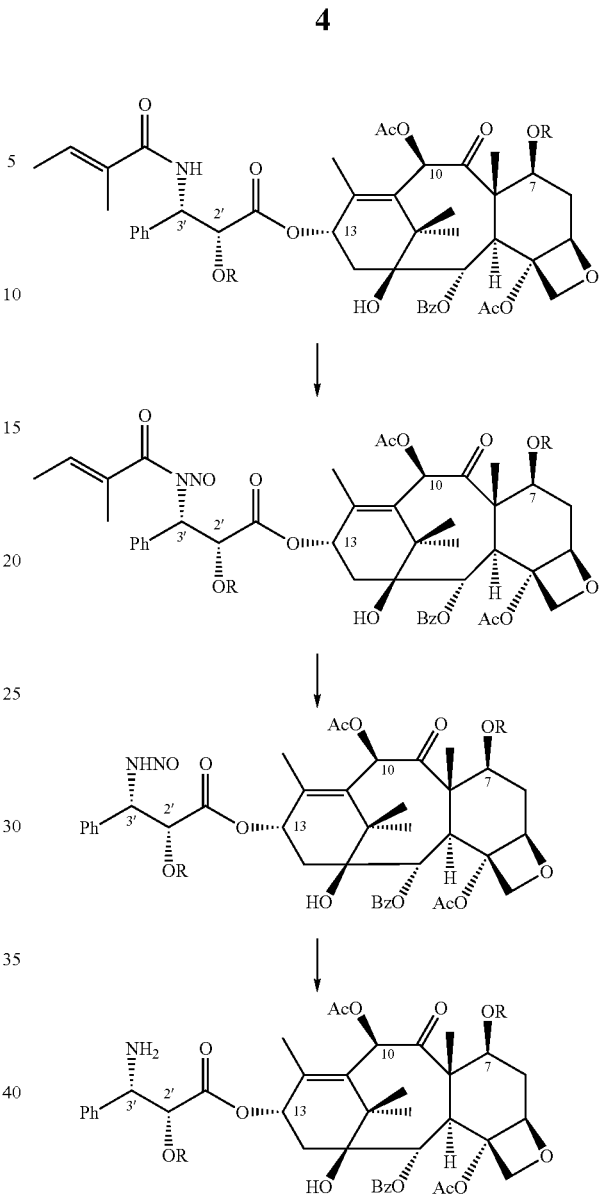

wherein R is at each occurrence independently selected from hydrogen and a hydroxy-protecting group.

In yet another alternate more specific embodiment, the step of converting cephalomannine to the taxane intermediate further comprises the steps of (1) converting cephalomannine to a cephalomannine epoxide analogue having the structure:

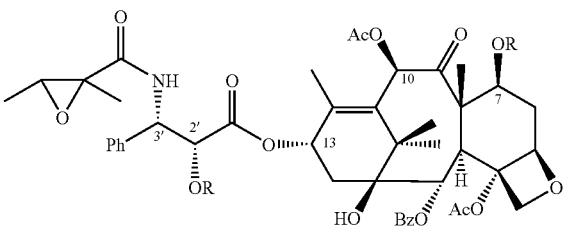

wherein R is at each occurrence independently selected from hydrogen and a hydroxy-protecting group, (2) converting the cephalomannine epoxide analogue to a cephalomannine azido alcohol analogue having the structure:

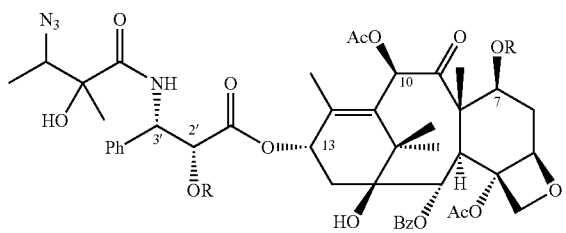

wherein R is at each occurrence independently selected from hydrogen and a hydroxy-protecting group, and (3) converting the cephalomannine azido alcohol analogue to the taxane intermediate.

In a second embodiment, the present invention provides a process for preparing a taxane comprising the steps of (1) converting cinnamoyl halide to a cinnamoyl halide aziridine intermediate having the structure:

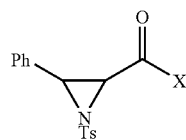

wherein X is halogen, (2) reacting the cinnamoyl halide aziridine intermediate with protected baccatin III to provide a protected baccatin III aziridine intermediate having the structure:

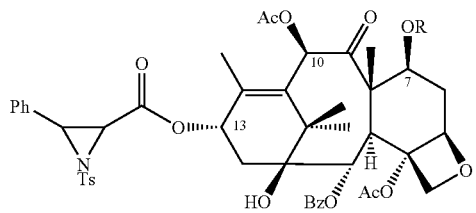

wherein R is selected from hydrogen and a hydroxy-protecting group, (3) converting the protected baccatin III aziridine intermediate to a taxane intermediate having the structure:

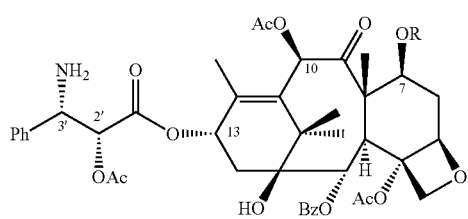

wherein R is selected from hydrogen and a hydroxy-protecting group, and (4) converting the taxane intermediate to paclitaxel or docetaxel.

In a more specific embodiment of the foregoing process X is chloro.

In a third embodiment, the present invention provides a process for preparing a taxane comprising the steps of (1) converting cinnamoyl halide to a cinnamoyl halide aziridine intermediate having the structure:

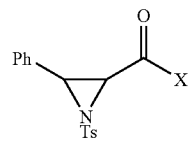

wherein X is halogen, (2) converting the cinnamoyl halide aziridine intermediate to an open chain cinnamoyl halide intermediate having the structure:

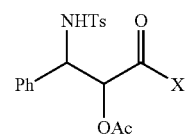

wherein X is halogen, (3) reacting the open chain cinnamoyl halide intermediate with protected baccatin III to provide a protected baccatin III intermediate having the structure:

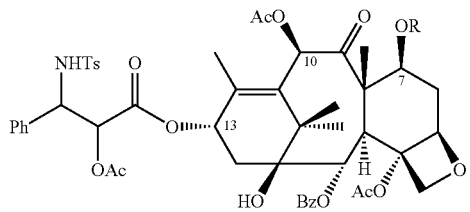

wherein R is selected from hydrogen and a hydroxy-protecting group, (4) converting the protected baccatin III intermediate to a taxane intermediate having the structure:

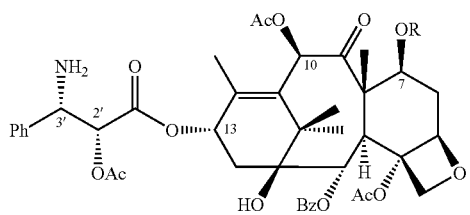

wherein R is selected from hydrogen and a hydroxy-protecting group, and (5) converting the taxane intermediate to paclitaxel or docetaxel.

In a more specific embodiment of the foregoing process, the step of reacting the open chain cinnamoyl halide intermediate with protected baccatin III further comprises the steps of (1) converting the open chain cinnamoyl halide intermediate to a β-lactam intermediate having the structure:

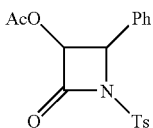

and (2) reacting the β-lactam intermediate with protected baccatin III to provide the protected baccatin III intermediate.

In another more specific embodiment of the foregoing process X is chloro.

In a fourth embodiment, the present invention provides a process for preparing docetaxel from cephalomannine comprising the reaction sequence:

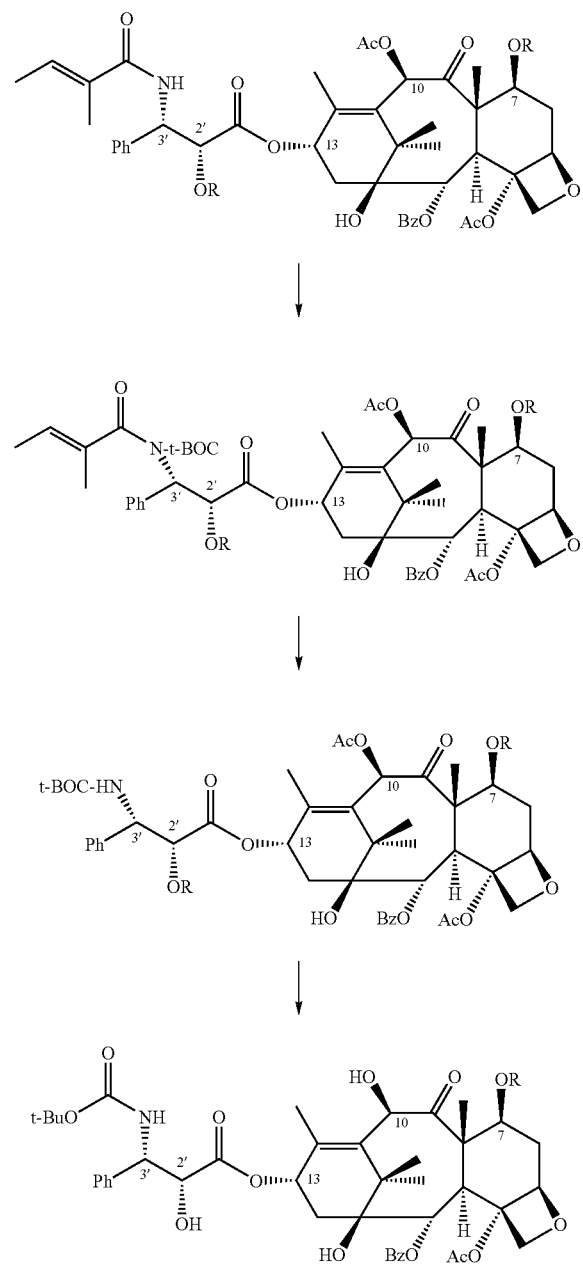

wherein R is at each occurrence independently selected from hydrogen and a hydroxy-protecting group.

These and other aspects of the invention will be apparent upon reference to the attached figures and following detailed description.

DETAILED DESCRIPTION OF THE INVENTION

Figure 1:
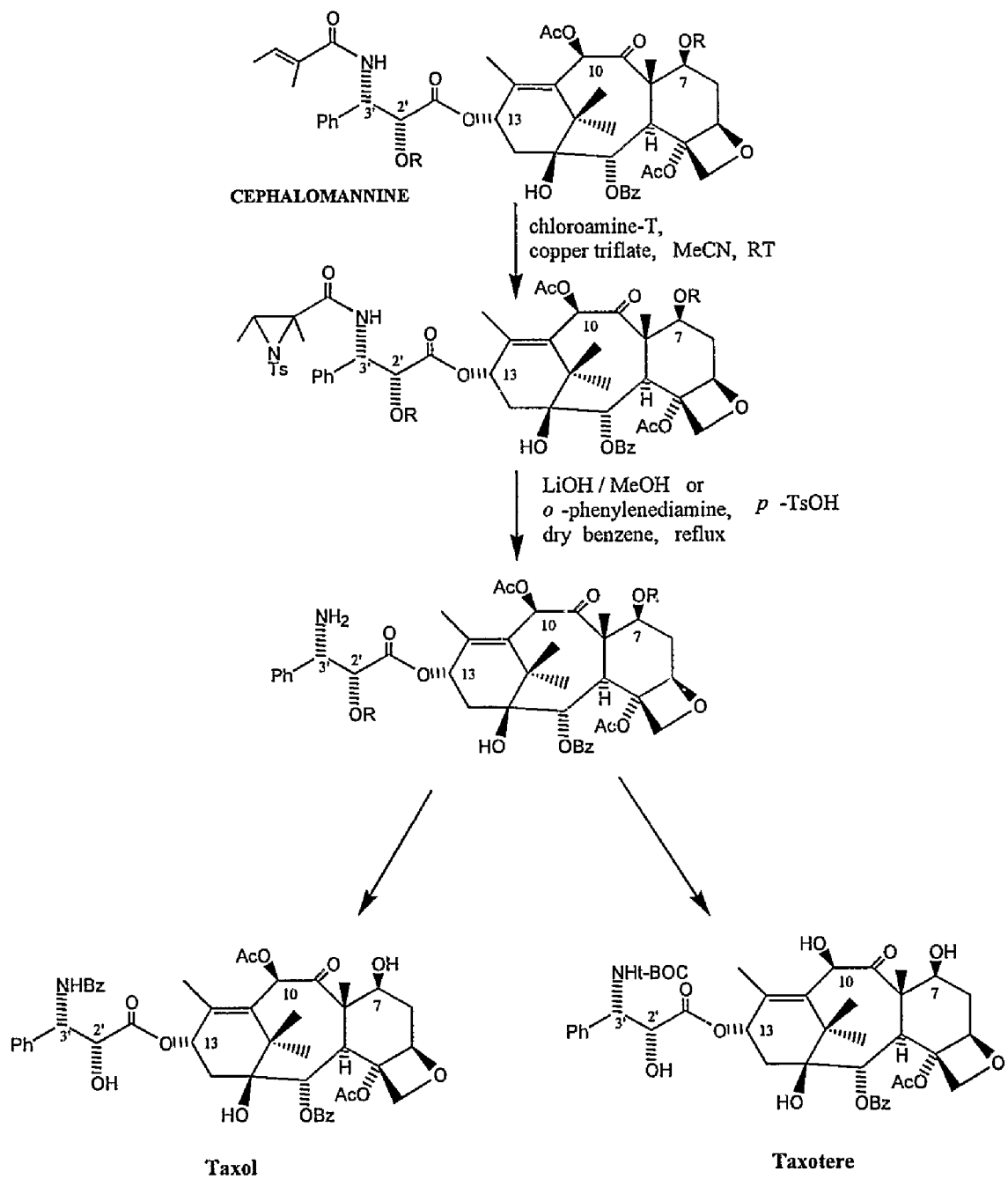
FIGS. 1, 2, 3, 4, 5, 6, 7 and 8 illustrate chemical routes for the preparation of taxane intermediates and aziridine analogues, and their conversion to paclitaxel and docetaxel according to the present invention.

As noted above, the present invention relates to the semisynthesis of novel taxane intermediates and aziridine analogues, in particular, aziridine analogues of cephalomannine and baccatin III intermediates, and their conversion to active antitumor agents, paclitaxel and docetaxel.

As used herein, the term "hydroxy-protecting group" refers to a readily cleavable group bonded to the oxygen of a hydroxy (—OH) group. Examples of hydroxy protecting groups include, without limitation, acetyl (Ac), benzyl (PhCH$_2$), 1-ethoxyethyl (EE), methoxymethyl (MOM), (methoxyethoxy)methyl (MEM), (p-methoxyphenyl)methoxymethyl (MPM), tert-butyldimethylsilyl (TBS), tert-butyldiphenylsilyl (TBPS), tert-butoxycarbonyl (tBoc, t-Boc, tBOC, t-BOC), tetrahydropyranyl (THP), triphenylmethyl (Trityl, Tr), 2-methoxy-2-methylpropyl, benzyloxycarbonyl (Cbz), trichloroacetyl (OCCCl$_3$), 2,2,2-trichloroethoxycarbonyl (Troc), benzyloxymethyl (BOM), tert-butyl (t-Bu), triethylsilyl (TES), trimethylsilyl (TMS), and triisopropylsilyl (TIPS). The related term "protected hydroxy group" refers to a hydroxy group that is bonded to a hydroxy-protecting group. General examples of protected hydroxy groups include, without limitation, —O-alkyl, —O-acyl, acetal, and —O-ethoxyethyl, where some specific protected hydroxy groups include, formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformoxy, p-nitro benzoyloxy, ethoxycarbonyloxy, methoxycarbonyloxy, propoxycarbonyloxy, 2,2,2-trichloro ethoxycarbonyloxy, benzyloxycarbonyloxy, tert-butoxycarbonyloxy, 1-cyclopropyl ethoxycarbonyloxy, phthaloyloxy, butyryloxy, isobutyryloxy, valeryloxy, isovaleryloxy, oxalyoxy, succinyloxy and pivaloyloxy, phenylacetoxy, phenylpropionyloxy, mesyloxy, chlorobenzoyloxy, para-nitrobenzoyloxy, para-tert-butyl benzoyloxy, capryloyloxy, acryloyloxy, methylcarbamoyloxy, phenylcarbamoyloxy, naphthylcarbamoyloxy, and the like. Hydroxyprotecting groups and protected hydroxy groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

The following Table shows the chemical structure of some hydroxy-protecting groups, as well as nomenclature used to identify those chemical structures.

TABLE 1

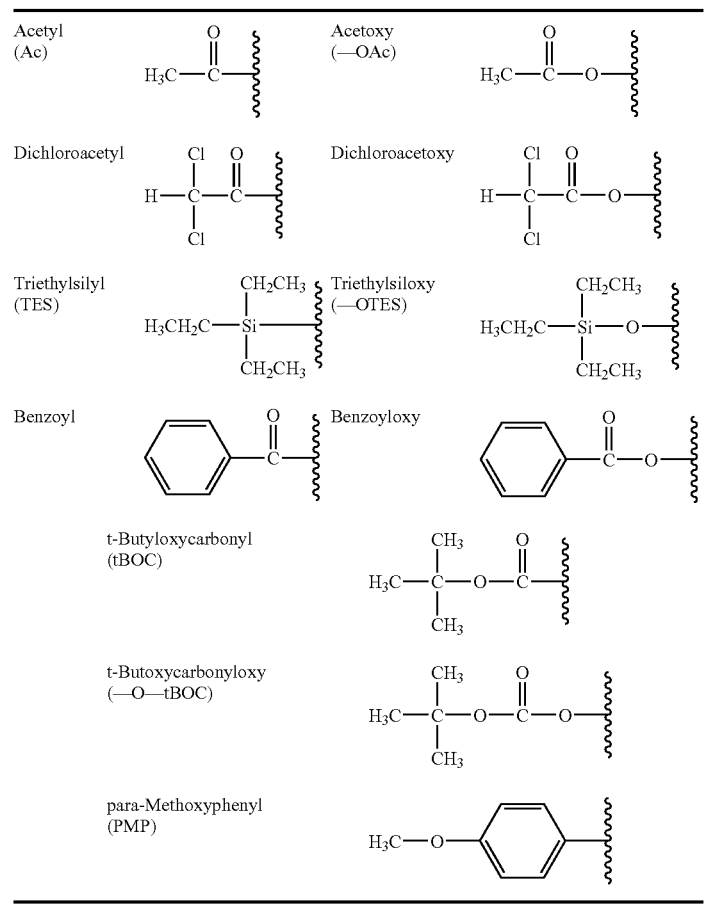

The term "alkyl" refers to a hydrocarbon structure wherein the carbons are arranged in a linear, branched, or cyclic manner, including combinations thereof. Lower alkyl refers to alkyl groups of from 1 to 5 carbon atoms. Examples of lower alkyl groups include methyl, ethyl, propyl, isopropyl, butyl, s- and t-butyl and the like. "Cycloalkyl" is a subset of alkyl and includes cyclic hydrocarbon groups of from 3 to 13 carbon atoms. Examples of cycloalkyl groups include cyclopropyl, cyclobutyl, cyclopentyl, norbornyl, adamantyl and the like. When an alkyl residue having a specific number of carbons is named, all geometric isomers having that number of carbons are intended to be encompassed; thus, for example, "butyl" is meant to include n-butyl, sec-butyl, isobutyl and t-butyl; propyl includes n-propyl and isopropyl.

The term "alkenyl" refers to an alkyl group having at least one site of unsaturation, i.e., at least one double bond.

The term "alkynyl" refers to an alkyl group having at least one triple bond between adjacent carbon atoms.

The terms "alkoxy" and "alkoxyl" both refer to moieties of the formula —O-alkyl. Examples include methoxy, ethoxy, propoxy, isopropoxy, cyclopropyloxy, cyclohexyloxy and the like. Lower-alkoxy refers to groups containing one to four carbons. The analogous term "aryloxy" refers to moieties of the formula —O-aryl.

The term "acyl" refers to moieties of the formula —C(=O)-alkyl. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

The term "aryl" refers to phenyl or naphthyl. Substituted aryl refers to mono- and poly-substituted phenyl or naphthyl. Exemplary substituents for aryl include one or more of halogen, hydroxyl, alkoxy, aryloxy, heteroaryloxy, amino, alkylamino, dialkylamino, mercapto, alkylthio, arylthio, heteroarylthio, cyano, carboxyl, alkoxycarbonyl where the alkoxy portion contains 1 to 15 carbons, aryloxycarbonyl where the aryloxy portion contains 6 to 20 carbon, or heteroarylcarbonyl where the heteroaryl portion contains 3 to 15 carbon atoms.

The term "heteroaryl" refers to a 5- or 6-membered heteroaromatic ring containing 1-3 heteroatoms selected from O, N, or S; a bicyclic 9- or 10-membered heteroaromatic ring system containing 0-3 heteroatoms selected from O, N, or S; or a tricyclic 13- or 14-membered heteroaromatic ring system containing 0-3 heteroatoms selected from O, N, or S. Exemplary aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

The term "halogen" refers to fluoro, chloro, bromo or iodo.

In a first embodiment, the present invention provides a process for preparing a taxane comprising the steps of (1) converting cephalomannine to a primary amine taxane intermediate having the structure:

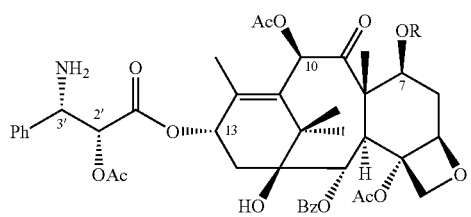

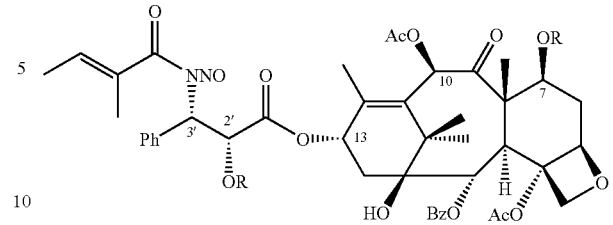

wherein R is at each occurrence independently selected from hydrogen and a hydroxy-protecting group, and (2) converting the taxane intermediate to paclitaxel or docetaxel.

In a more specific embodiment, cephalomannine is converted to a cephalomannine aziridine analogue having the structure:

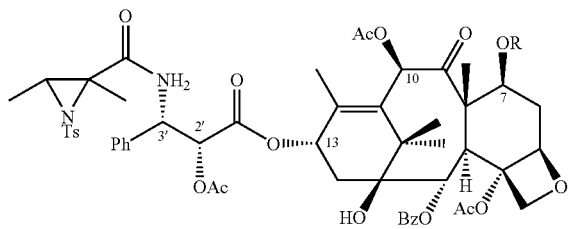

wherein R is at each occurrence independently selected from hydrogen and a hydroxy-protecting group, by substituting the double bond of the C-13 side chain of cephalomannine with an aziridine ring. The cephalomannine aziridine analogue is subsequently hydrolyzed to give the primary amine taxane intermediate.

In an alternate more specific embodiment, cephalomannine is directly hydrolyzed with formic acid to give the primary amine taxane intermediate.

In yet another alternate more specific embodiment, cephalomannine is converted to the primary amine taxane intermdiate by nitrosation using sodium nitrite in AcOH:Ac$_2$O or N$_2$O$_4$ in acetonitrile, followed by lithium hydroxide and 30% hydrogen peroxide hydrolysis and, then, Raney-Nickel reduction according to the reaction sequence:

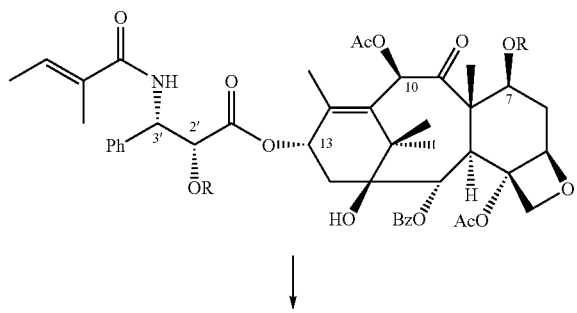

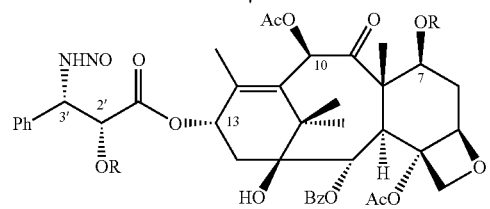

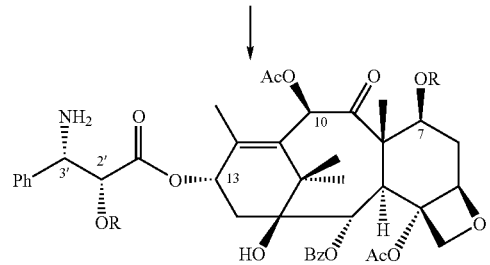

wherein R is at each occurrence independently selected from hydrogen and a hydroxy-protecting group.

In yet another alternate more specific embodiment, cephalomannine is converted to a cephalomannine epoxide analogue having the structure:

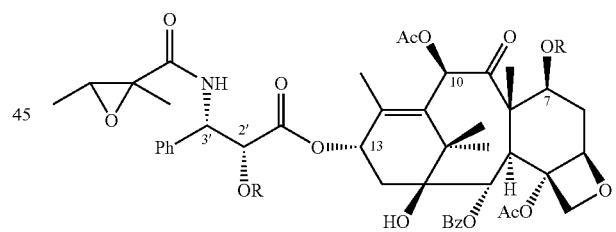

wherein R is at each occurrence independently selected from hydrogen and a hydroxy-protecting group, which is then reacted with sodium azide in methanol at 65° C. to give a cephalomannine azido alcohol analogue having the structure:

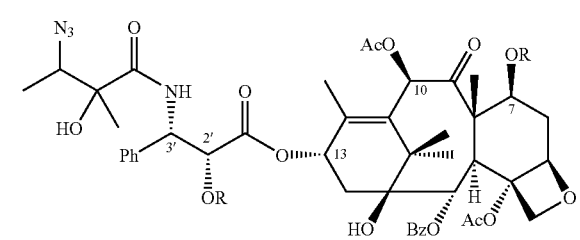

wherein R is at each occurrence independently selected from hydrogen and a hydroxy-protecting group, which is then reduced to the give the primary amine taxane intermediate.

In a second embodiment, the present invention provides a process for preparing a taxane comprising the steps of (1) converting cinnamoyl halide to a cinnamoyl halide aziridine intermediate having the structure:

wherein X is halogen, (2) coupling the cinnamoyl halide aziridine intermediate with protected baccatin III using NaH, DCM to provide a protected baccatin III aziridine intermediate having the structure:

wherein R is selected from hydrogen and a hydroxy-protecting group, (3) hydrolyzing the protected baccatin III aziridine intermediate to a taxane intermediate having the structure:

wherein R is selected from hydrogen and a hydroxy-protecting group, and (4) converting the taxane intermediate to paclitaxel or docetaxel.

In a more specific embodiment of the foregoing process, X is chloro.

In a third embodiment, the present invention provides a process for preparing a taxane comprising the steps of (1) converting cinnamoyl halide to a cinnamoyl halide aziridine intermediate having the structure:

wherein X is halogen, (2) reacting the cinnamoyl halide aziridine intermediate with acetic acid to give an open chain cinnamoyl halide intermediate having the structure:

wherein X is halogen, (3) coupling the open chain cinnamoyl halide intermediate with protected baccatin III using NaH, DCM to provide a protected baccatin III intermediate having the structure:

wherein R is selected from hydrogen and a hydroxy-protecting group, (4) hydrolyzing the protected baccatin III intermediate to a taxane intermediate having the structure:

wherein R is selected from hydrogen and a hydroxy-protecting group, and (5) converting the taxane intermediate to paclitaxel or docetaxel.

In a more specific embodiment of the foregoing process, the step of reacting the open chain cinnamoyl halide intermediate with protected baccatin III further comprises the steps of (1) converting the open chain cinnamoyl halide intermediate to a β-lactam intermediate having the structure:

and (2) reacting the β-lactam intermediate with protected baccatin III to provide the protected baccatin III intermediate.

In another more specific embodiment of the foregoing process, X is chloro.

In a fourth embodiment, the present invention provides a process for preparing docetaxel from cephalomannine by introduction of a t-BOC group at the secondary amine of protected cephalomannine followed by hydrolysis with lithium hydroxide in THF, and deprotection at the 2', 7 and 10 positions according to the reaction sequence:

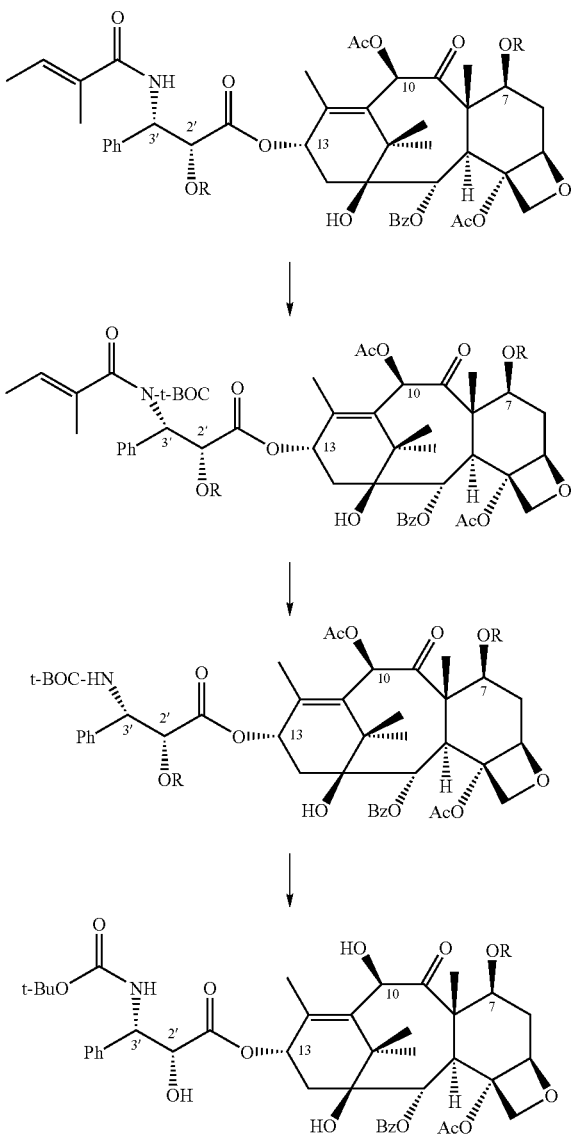

wherein R is at each occurrence independently selected from hydrogen and a hydroxy-protecting group.

EXAMPLES

The following Examples disclose specific processes for synthesizing various aziridine analogues, and their conversion to paclitaxel and docetaxel. The disclosed processes may be utilized with both purified and partially purified taxanes. Unless otherwise noted, all scientific and technical terms have the meanings as understood by one of ordinary skill in the art.

Example 1

Aziridination of Cephalomannine

As shown in FIG. 1, cephalomannine (0.12 mmol) was dissolved in dry freshly distilled acetonitrile (1 ml) at room temperature under anhydrous conditions. To this solution was added chloroamine-T (0.18 mmol), followed by copper triflate (0.12 mmol) with vigorous stirring. The mixture was stirred under slightly warming (25° C.) conditions until all starting material were consumed. The mixture was worked up and purified by column chromatography using mixtures of dichloromethane and ethyl acetate to give white crystals of the cephalomannine aziridine analogue.

Preparation of Primary Amine Taxane Intermediate

Process 1. To a solution of the above cephalomannine aziridine analogue (0.025 mmol) in dry benzene (5 ml) were added o-phenylenediamine (0.025 mmol) and p-toluenesulfonic acid (catalytic, 2 mg). The mixture was refluxed for 16 h until all starting material was consumed (TLC). The mixture was allowed to cool to room temperature, diluted with ethyl acetate and washed successively with dilute HCl (1N) followed by water and brine. The organic layer was dried and purified by column chromatography using mixtures of dichloromethane and ethyl acetate to yield the primary amine taxane intermediate.

Process 2. To a 0.2 M solution of the above cephalomannine aziridine analogue (3.51 mmol) in tetrahydrofuran was added 10.54 ml (10.54 mmol) of a 1.0 N solution of lithium hydroxide. The solution was stirred for 12 h at room temperature. After removal of tetrahydrofuran in vacuo, the basic aqueous residue was acidified by the addition of 10% acetic acid and extracted with ether. Drying (MgSO$_4$) and concentration afforded the crude material that was purified by column chromatography to afford the pure white solid of the primary amine taxane intermediate. (Note: The following could also be used: 10 equiv. LiOH, 20 equiv. 30% H$_2$O$_2$, 3:1 THF:H$_2$O, time, 0⇒T ° C.; Na$_2$SO$_3$, 5 min. 0° C.).

Conversion of Primary Amine Taxane Intermediate to Paclitaxel or Docetaxel

A sample of the primary amine taxane intermediate (0.091 mmol) was dissolved in ethyl acetate (9.1 ml) and a saturated solution of NaHCO$_3$ (9.1 ml) was added. To this biphasic mixture was added di-tert-butyl dicarbonate (0.18 mmol). The mixture was stirred for 12 h at room temperature and TLC showed complete consumption of the starting material. The reaction was worked up as usual and the residue purified by column chromatography using mixtures of dichloromethane and ethyl acetate or acetone to give docetaxel. The $^1$H NMR, $^{13}$C NMR and mass spectra data for the isolated material match with the reported data for docetaxel.

To convert the primary amine to taxol, there are several methods that could be used, such as the method disclosed in U.S. Pat. No. 5,808,113, which is incorporated herein by reference in its entirety.

Example 2

Hydrolysis of Cephalomannine

Figure 2:
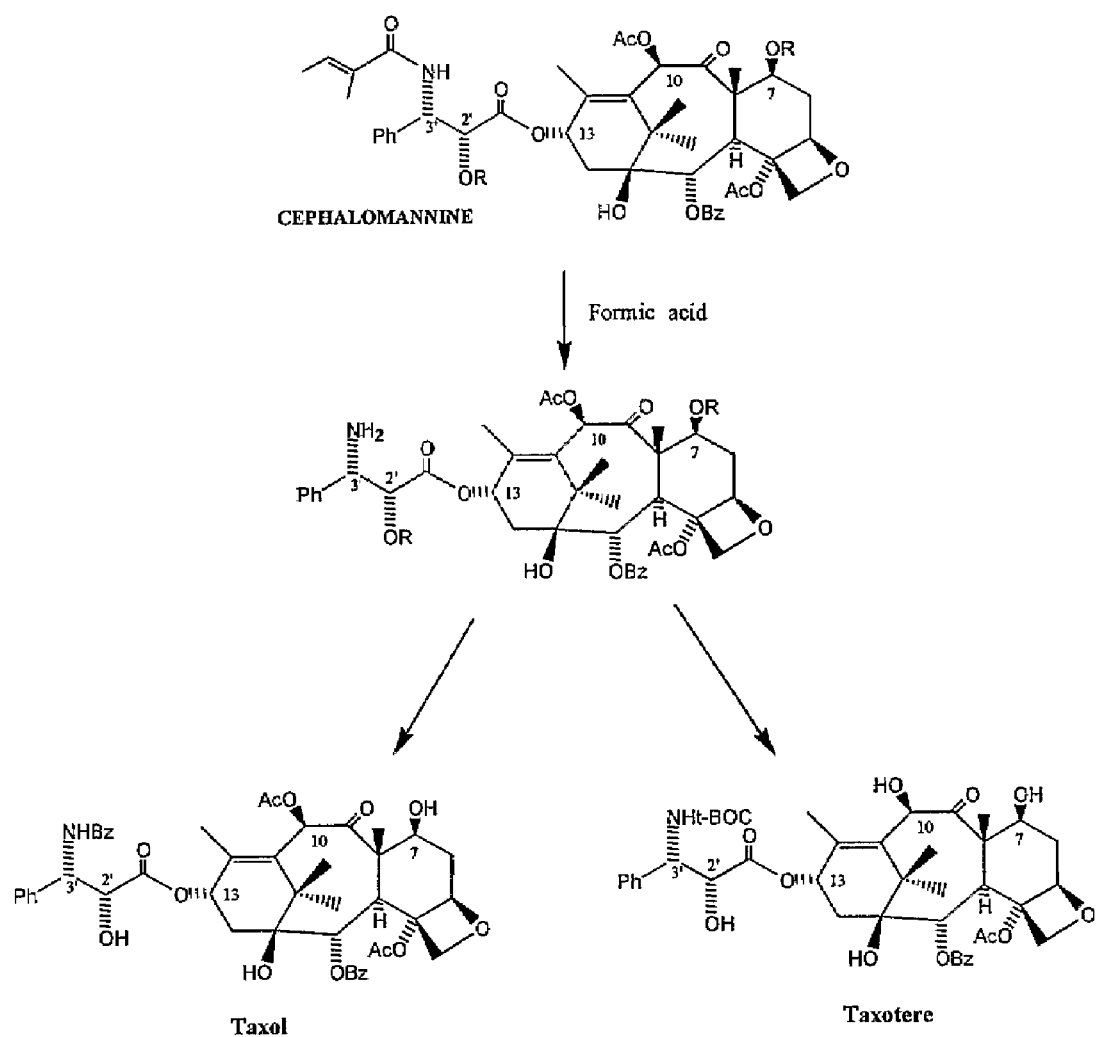

As shown in FIG. 2, cephalomannine was dissolved in formic acid at 0° C., stirred at this temperature for 12 h, poured over crushed ice and worked up as usual. The crude residue was purified by column chromatography using mixtures of dichloromethane and ethyl acetate to afford the pure primary amine taxane intermediate.

Example 3

Aziridination of Cinnamoyl Chloride

Figure 3:
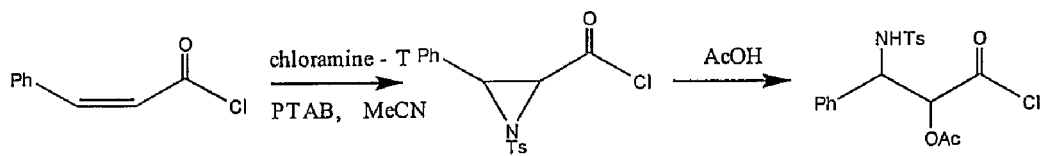

As shown in FIG. 3, to a mixture of cinnamoyl chloride and anhydrous chloramine-T in acetonitrile was added phenyltrimethylammonium tribromide (PTAB) at room temperature. After 12 h of vigorous stirring, the reaction mixture was concentrated and filtered through a short column of silica gel and eluted with 10% ethyl acetate in hexanes. After evaporation of the solvent, the resultant solid was purified by column chromatography or recrystallization to afford the cinnamoyl chloride aziridine intermediate.

Acid-catalyzed Ring Opening

As further shown in FIG. 3, the cinnamoyl chloride aziridine intermediate was dissolved in aqueous acetic acid at 0° C., stirred at this temperature for 10 h and worked up as usual. Purification of the crude mixture by column chromatography and crystallization afforded the open chain cinnamoyl chloride intermediate.

Preparation of β-lactam Intermediate

Figure 4:
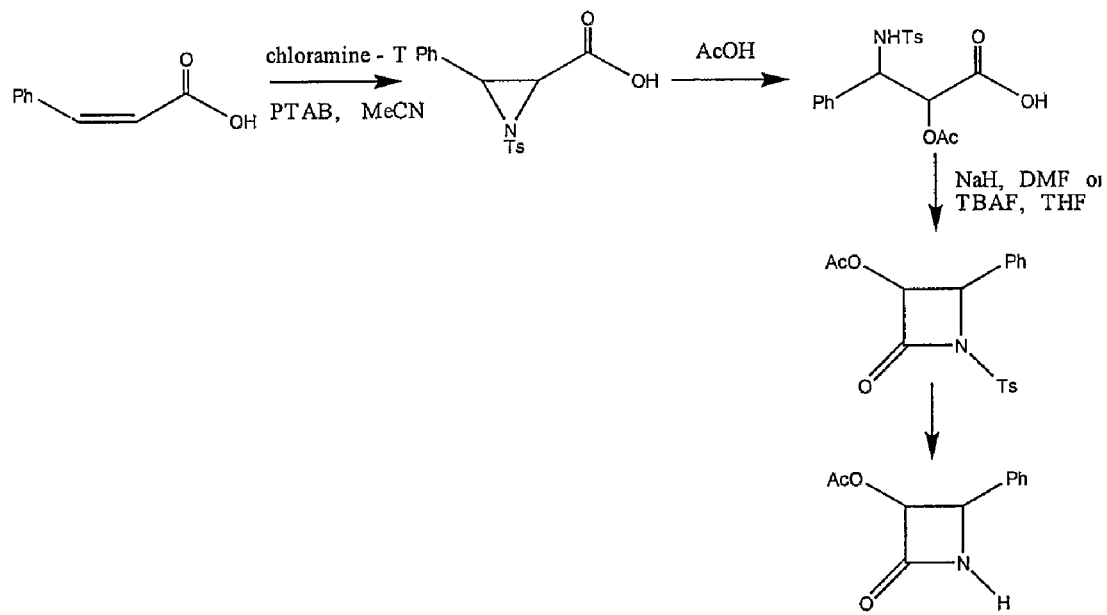

As shown in FIG. 4, the above open chain cinnamoyl chloride intermediate was cyclized to form the β-lactam intermediate using methods well known in the literature.

Example 4

Coupling Reaction

Figure 5:
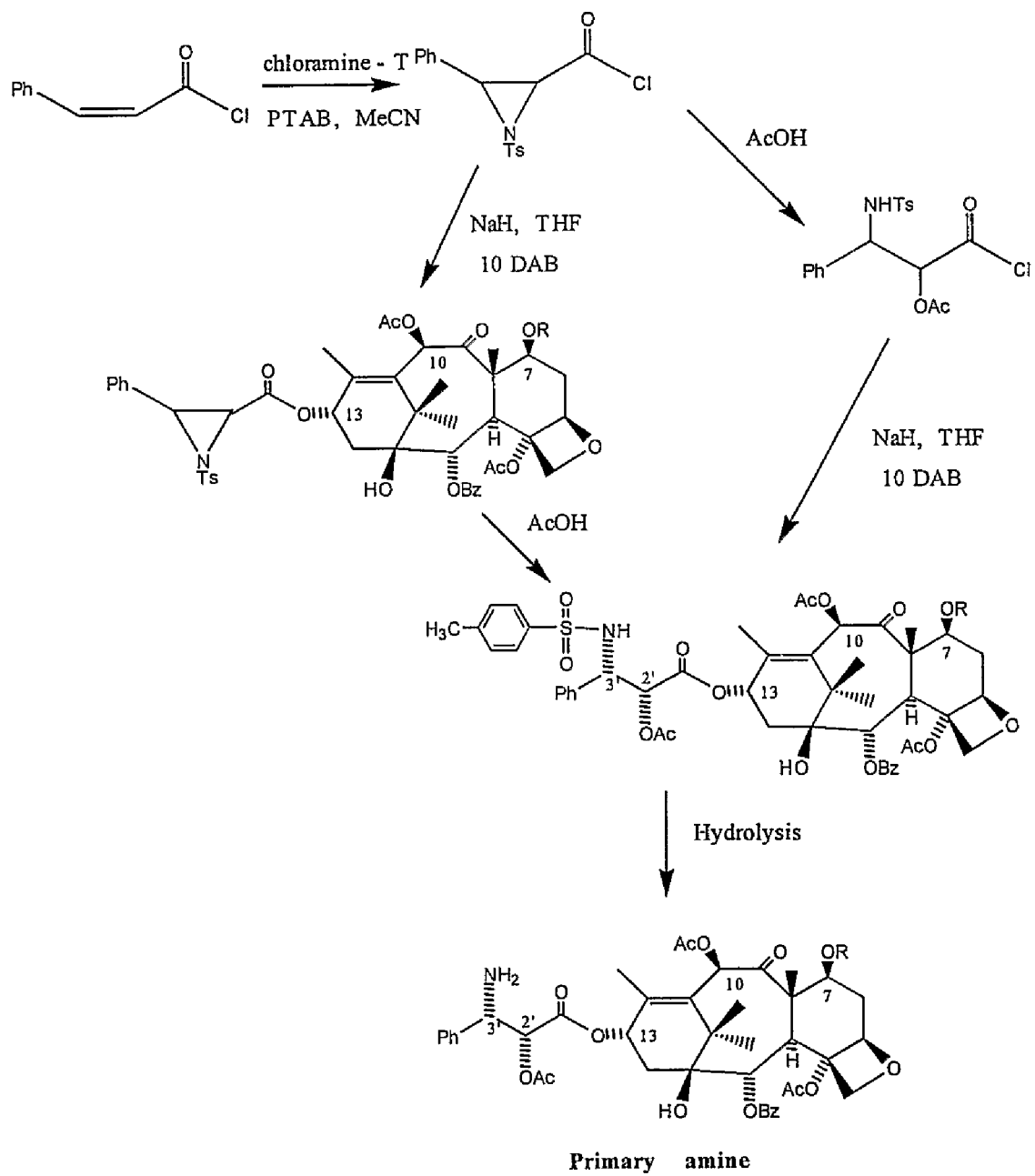

As shown in FIG. 5, the open chain cinnamoyl chloride intermediate and C7 protected baccatin III were dissolved in anhydrous freshly distilled THF under argon atmosphere at room temperature. The stirred solution was cooled to 0° C. and added to a suspension of NaH in THF at 0° C. The solution was warmed slowly to room temperature and maintained at this temperature for 3 h. The reaction mixture was cooled to 0° C. and quenched with brine. The reaction mixture was extracted with dichloromethane and the combined extracts were washed several times with brine, dried over anhydrous sodium sulfate, and concentrated under reduced pressure to give the crude product. The crude product was purified by column chromatography using mixtures of hexanes and ethyl acetate to afford the pure coupled protected baccatin III intermediate that could be hydrolyzed to give the primary amine taxane intermediate. Although this reaction is illustrated in FIG. 5 with sodium hydride, in other embodiments of the present invention the coupling may be performed in the presences of a metal alkoxide, e.g., sodium hexamethyldisalide or lewis acid.

Example 5

Nitrosation

Figure 6:
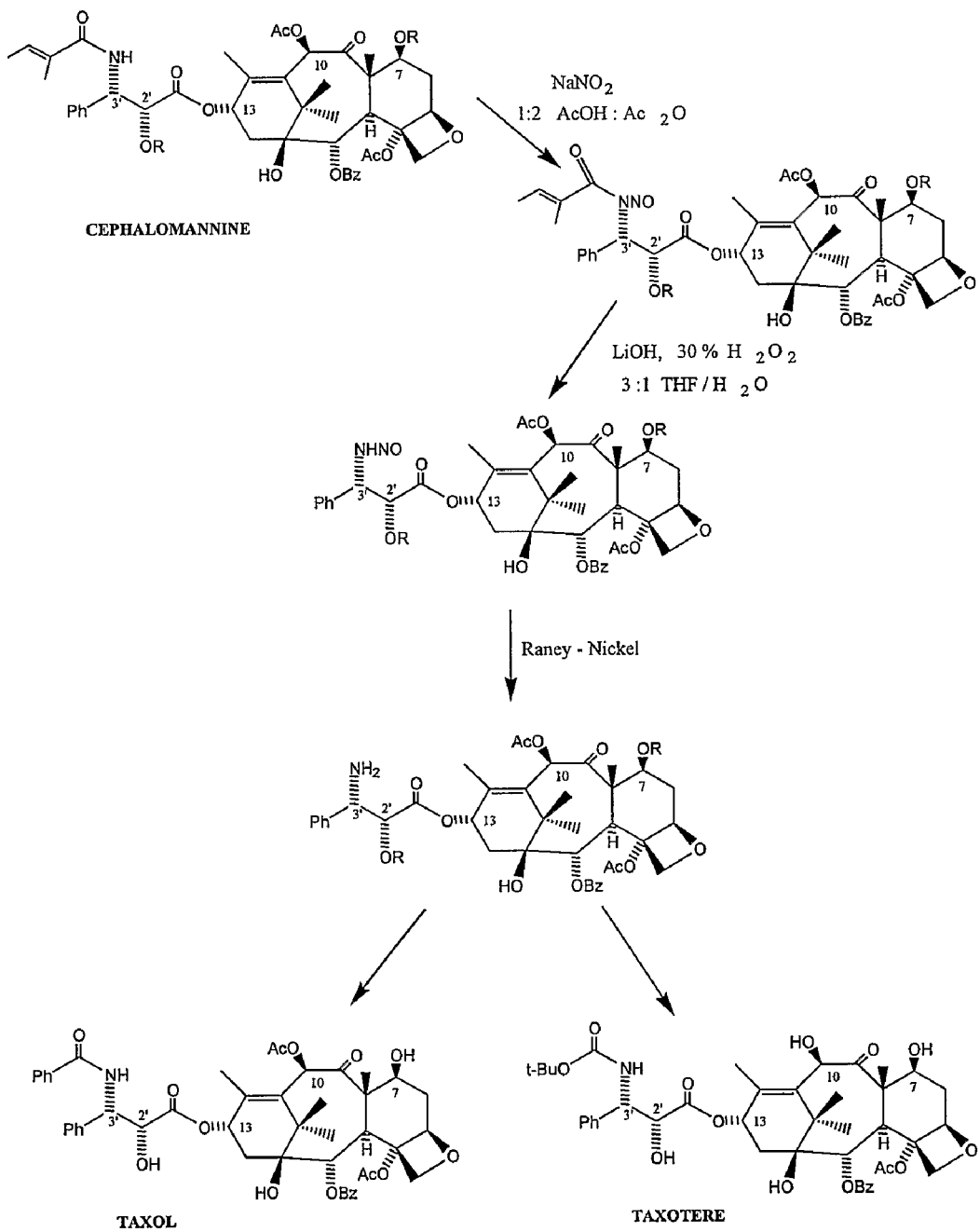

As shown in FIG. 6, to a solution of cephalomannine (0.76 mmol) in glacial acetic acid (2.5 ml) and acetic anhydride (5 ml) at 0° C. was added $NaNO_2$ (7.6 mmol). The resulting solution was stirred under argon at 0° C. for 16 h and then poured over ice and extracted with diethyl ether. The combined organic extracts were washed with water, 5% $Na_2CO_3$, water and saturated NaCl and dried over $MgSO_4$. The dry extracts were filtered and then concentrated in vacuo, and the crude product was purified by column chromatography using mixtures of hexane-ethyl acetate to afford the pure product.

Hydrolysis

To the above solution in tetrahydrofuran was added a 1.0 N solution of lithium hydroxide. The solution was stirred for 12 h at room temperature. After removal of tetrahydrofuran in vacuo, the basic aqueous residue was acidified by the addition of 10% acetic acid and extracted with ether. Drying ($MgSO_4$) and concentration afforded the crude material that was purified by column chromatography to afford the pure white solid of the primary amine taxane intermediate. (Note: The following could also be used: 10 equiv. LiOH, 20 equiv. 30% $H_2O_2$, 3:1 $THF:H_2O$, time, $0 \Rightarrow T$ ° C.; $Na_2SO_3$, 5 min. 0° C.).

Reduction

The above hydrolyzed product was dissolved in ethanol at room temperature and Raney-Nickel was added in one portion to the stirred solution. The reaction mixture was stirred at this temperature and treated with hydrogen, until the complete consumption of the starting material. The reaction mixture was filtered and the filtrate evaporated. The residue was dissolved in an inert solvent such as dichloromethane and worked up as usual. The crude product was purified by column chromatography using mixtures of dichloromethane and ethyl acetate to afford the pure product.

Example 6

Preparation of N-acyl Derivative

Figure 7:
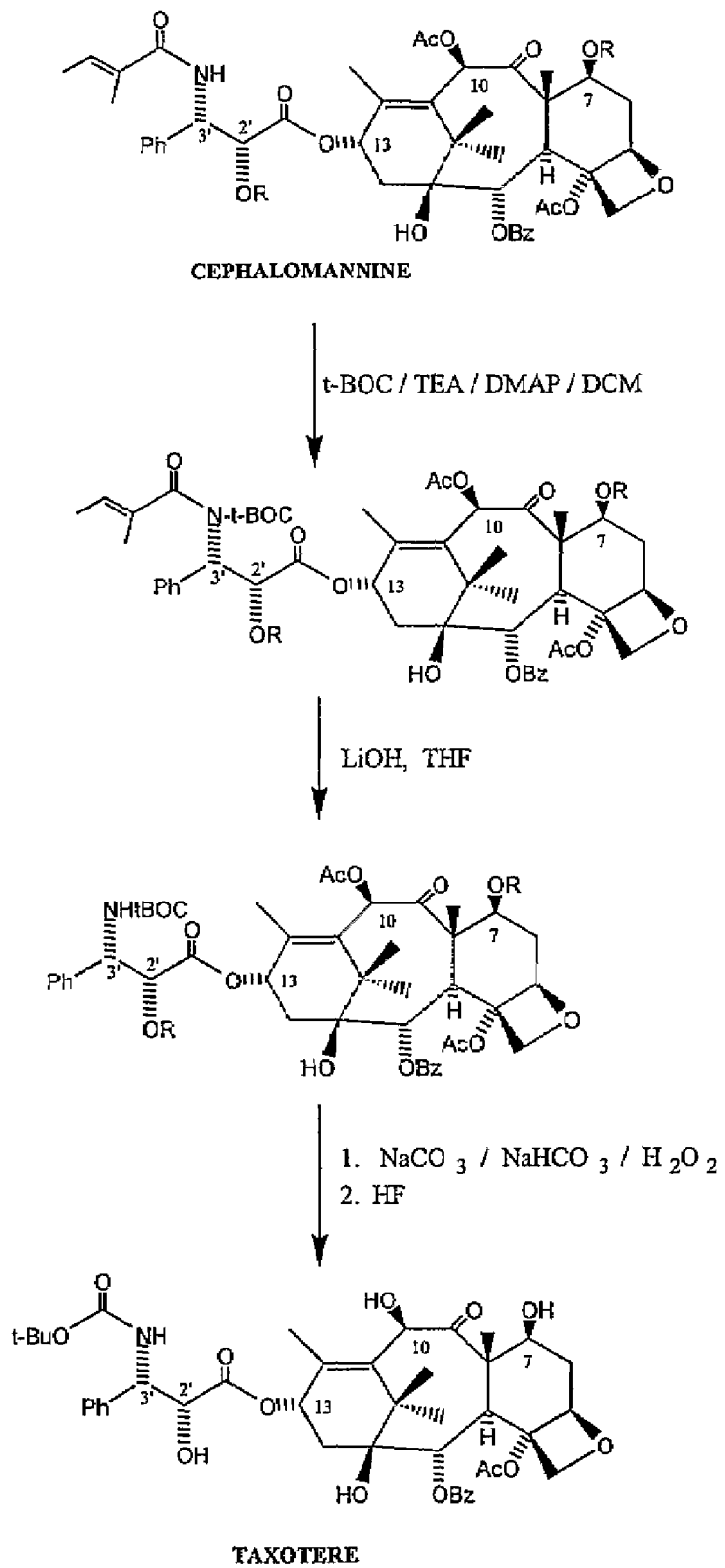

As shown in FIG. 7, to a solution of cephalomannine (9.47 mmol) in dichloromethane was added triethylamine (9.47 mmol), di-tert-butyl dicarbonate (18.94 mmol), and 4-(dimethylamino)pyridine (DMAP) (9.47 mmol). The solution was stirred for 12 h at room temperature under an argon atmosphere. The volatiles were removed and the residue was purified by column chromatography. Elution with dichloromethane and ethyl acetate afforded the cephalomannine N-t-BOC derivative.

Alternatively, DMAP (0.1 mmol) was added to a stirred solution of the cephalomannine (1.0 mmol) in dry acetonitrile followed by $BOC_2O$ (1.1 mmol). After stirring for 10 h at room temperature, all starting material was consumed (TLC). The reaction mixture was evaporated at room temperature and the residue partitioned between ether and aqueous $KHSO_4$. The organic extract was thoroughly washed in turn with aqueous solution of $KHSO_4$ and $NaHCO_3$ and finally brine and dried over $MgSO_4$. Evaporation to complete dryness left a light yellow residue that was purified by column chromatography to afford the cepahlomannine N-t-BOC derivative.

Example 7

Preparation of Cephalomannine Epoxide Analogue

Figure 8:
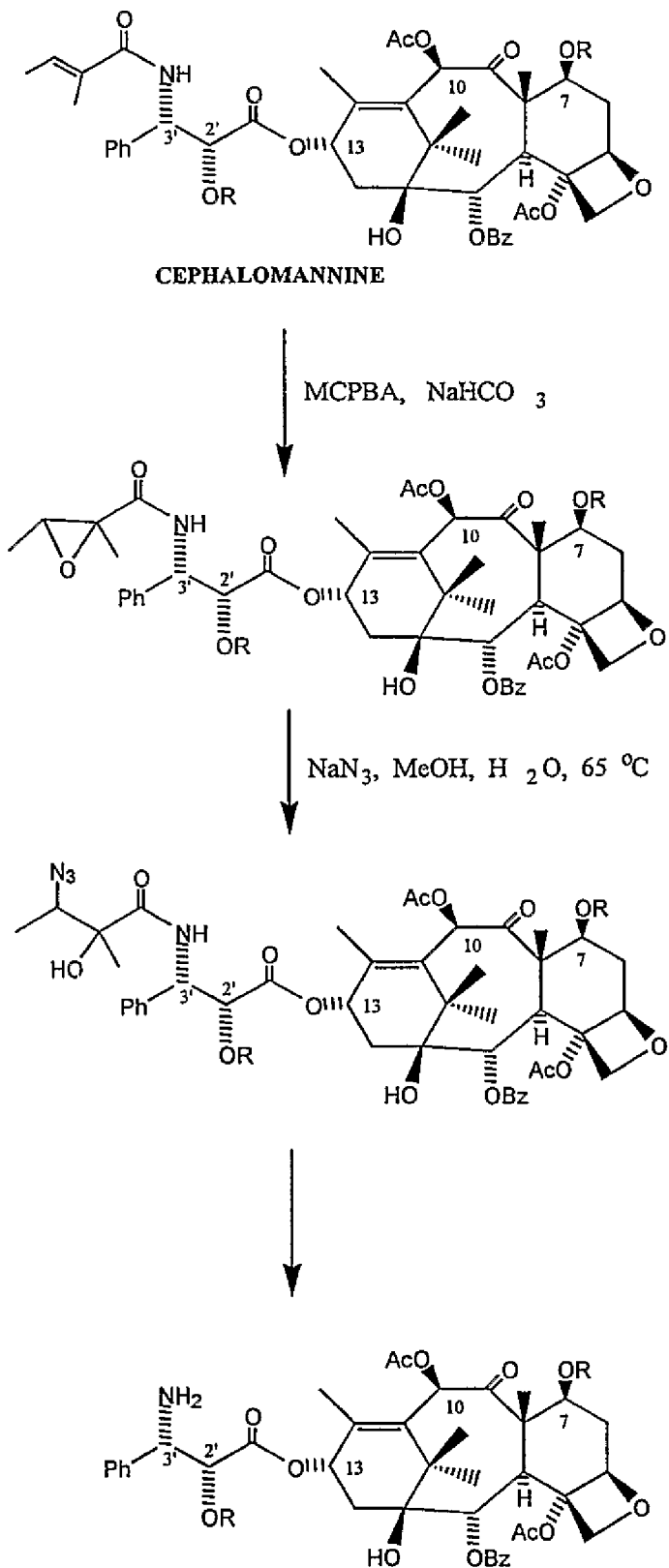

As shown in FIG. 8, to a solution of cephalomannine in dichloromethane was added $NaHCO_3$ followed by MCPBA at −15° C. The reaction was worked up as usual after the consumption of the starting material and purified by column chromatography using mixtures of dichloromethane and ethyl acetate to afford the pure cephalomannine epoxide analogue.

Preparation of Cepahlomannine Azido Alcohol Analogue

The cephalomannine epoxide analogue was dissolved in methanol and aqueous solution of $NaN_3$ was added at room temperature. The solution was heated to 65° C. for 12 h. The reaction mixture was cooled to room temperature and worked up as usual and purified by column chromatography using mixtures of dichloromethane and ethyl acetate to afford the pure cephalomannine azido alcohol analogue.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A process for preparing a taxane comprising the steps of:
converting cephalomannine to a taxane intermediate having the structure:

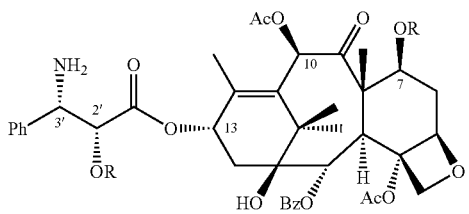

wherein R is at each occurrence independently selected from hydrogen and a hydroxy-protecting group; and
converting the taxane intermediate to paclitaxel or docetaxel, wherein the step of converting cephalomannine to the taxane intermediate further comprises the steps of:
converting cephalomannine to a cephalomannine aziridine analogue having the structure:

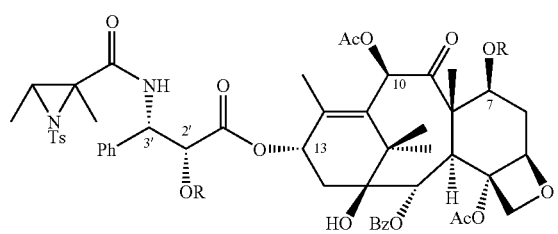

wherein R is at each occurrence independently selected from hydrogen and a hydroxyprotecting group; and
converting the cephalomannine aziridine analogue to the taxane intermediate.

2. The process of claim 1 wherein the taxane intermediate is converted to paclitaxel.

3. The process of claim 1 wherein the taxane intermediate is converted to docetaxel.

4. A process for preparing a taxane comprising the steps of:
converting cephalomannine to a taxane intermediate having the structure:

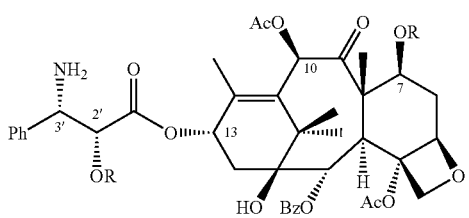

wherein R is at each occurrence independently selected from hydrogen and a hydroxyprotecting group; and
converting the taxane intermediate to paclitaxel or docetaxel, wherein the step of converting cephalomannine to the taxane intermediate comprises reacting cephalomannine with formic acid.

5. The process of claim 4 wherein the taxane intermediate is converted to paclitaxel.

6. The process of claim 4 wherein the taxane intermediate is converted to docetaxel.

7. A process for preparing a taxane comprising the steps of:
converting cephalomannine to a taxane intermediate having the structure:

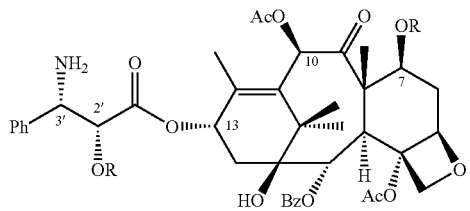

wherein R is at each occurrence independently selected from hydrogen and a hydroxy-protecting group; and
converting the taxane intermediate to paclitaxel or docetaxel, wherein the step of converting cephalomannine to the taxane intermediate further comprises the reaction sequence:

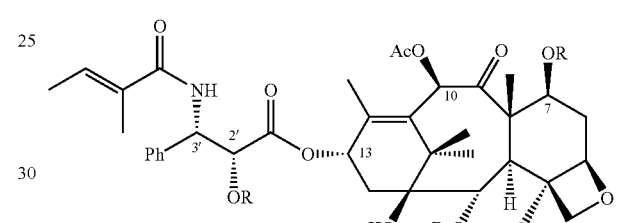

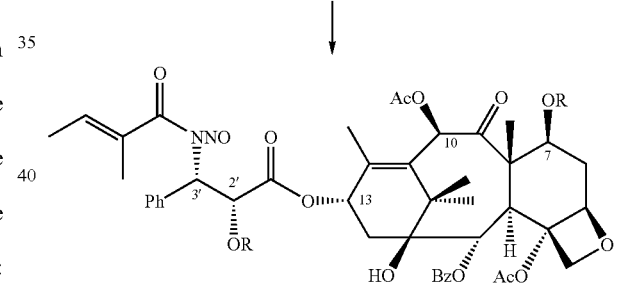

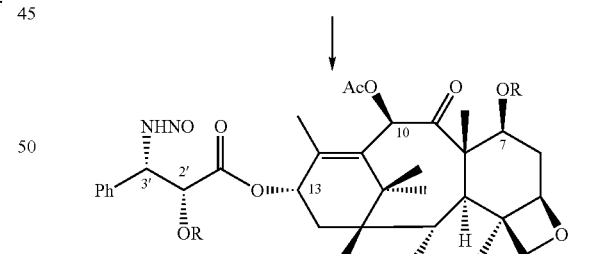

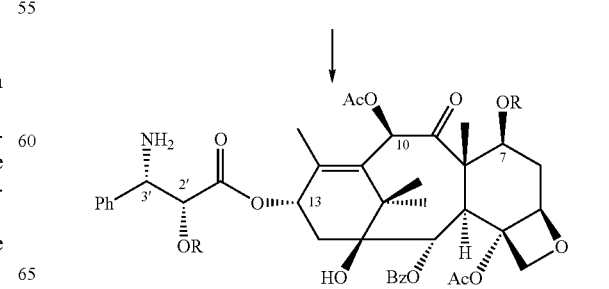

wherein R is at each occurrence independently selected from hydrogen and a hydroxy-protecting group.

8. The process of claim 7 wherein the taxane intermediate is converted to paclitaxel.

9. The process of claim 7 wherein the taxane intermediate is converted to docetaxel.

10. A process for preparing a taxane comprising the steps of:
converting cephalomannine to a taxane intermediate having the structure:

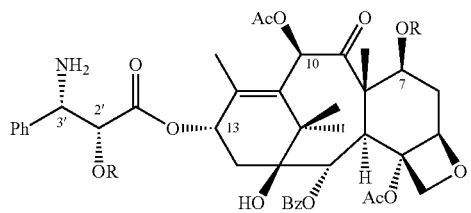

wherein R is at each occurrence independently selected from hydrogen and a hydroxy-protecting group; and
converting the taxane intermediate to paclitaxel or docetaxel, wherein the step of converting cephalomannine to the taxane intermediate further comprises the steps of:
converting cephalomannine to a cephalomannine epoxide analogue having the structure:

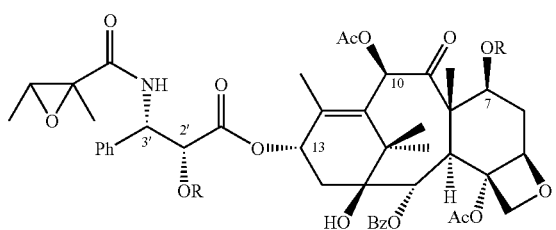

wherein R is at each occurrence independently selected from hydrogen and a hydroxy-protecting group;
converting the cephalomannine epoxide analogue to a cephalomannine azido alcohol analogue having the structure:

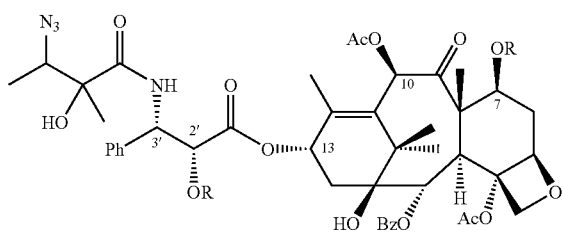

wherein R is at each occurrence independently selected from hydrogen and a hydroxy-protecting group; and
converting the cephalomannine azido alcohol analogue to the taxane intermediate.

11. The process of claim 10 wherein the taxane intermediate is converted to paclitaxel.

12. The process of claim 10 wherein the taxane intermediate is converted to docetaxel.

13. A process for preparing a taxane comprising the steps of:

converting cinnamoyl halide to a cinnamoyl halide aziridine intermediate having the structure:

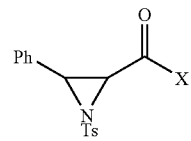

wherein X is halogen;
reacting the cinnamoyl halide aziridine intermediate with protected baccatin III to provide a protected baccatin III aziridine intermediate having the structure:

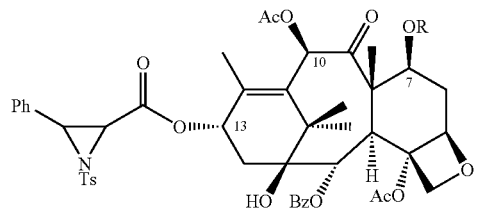

wherein R is selected from hydrogen and a hydroxy-protecting group;
converting the protected baccatin III aziridine intermediate to a taxane intermediate having the structure:

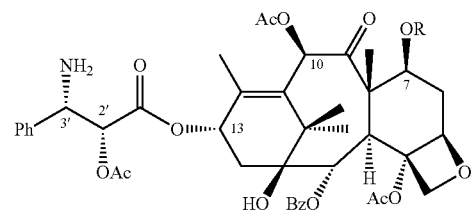

wherein R is selected from hydrogen and a hydroxy-protecting group; and
converting the taxane intermediate to paclitaxel or docetaxel.

14. The process of claim 13, wherein X is chloro.

15. A process for preparing a taxane comprising the steps of:
converting cinnamoyl halide to a cinnamoyl halide aziridine intermediate having the structure:

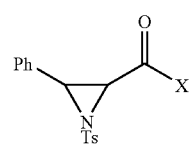

wherein X is halogen;
converting the cinnamoyl halide aziridine intermediate to an open chain cinnamoyl halide intermediate having the structure:

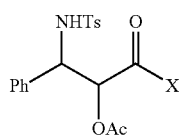

wherein X is halogen;
reacting the open chain cinnamoyl halide intermediate with protected baccatin III to provide a protected baccatin III intermediate having the structure:

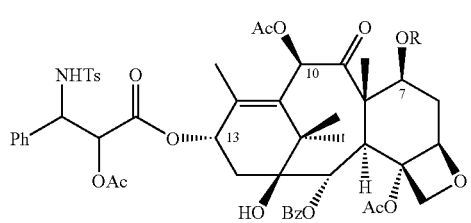

wherein R is selected from hydrogen and a hydroxy-protecting group;
converting the protected baccatin III intermediate to a taxane intermediate having the structure:

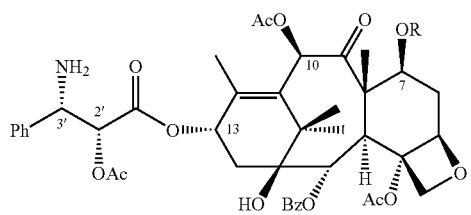

wherein R is selected from hydrogen and a hydroxy-protecting group; and converting the taxane intermediate to paclitaxel or docetaxel.

16. The process of claim 15, wherein X is chloro.

17. The process of claim 15, wherein the step of reacting the open chain cinnamoyl halide intermediate with protected baccatin III further comprises the steps of:
converting the open chain cinnamoyl halide intermediate to a β-lactam intermediate having the structure:

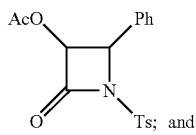 and reacting the β-lactam intermediate with protected baccatin III to provide the protected baccatin III intermediate.

18. A process for preparing docetaxel from cephalomannine comprising the reaction sequence:

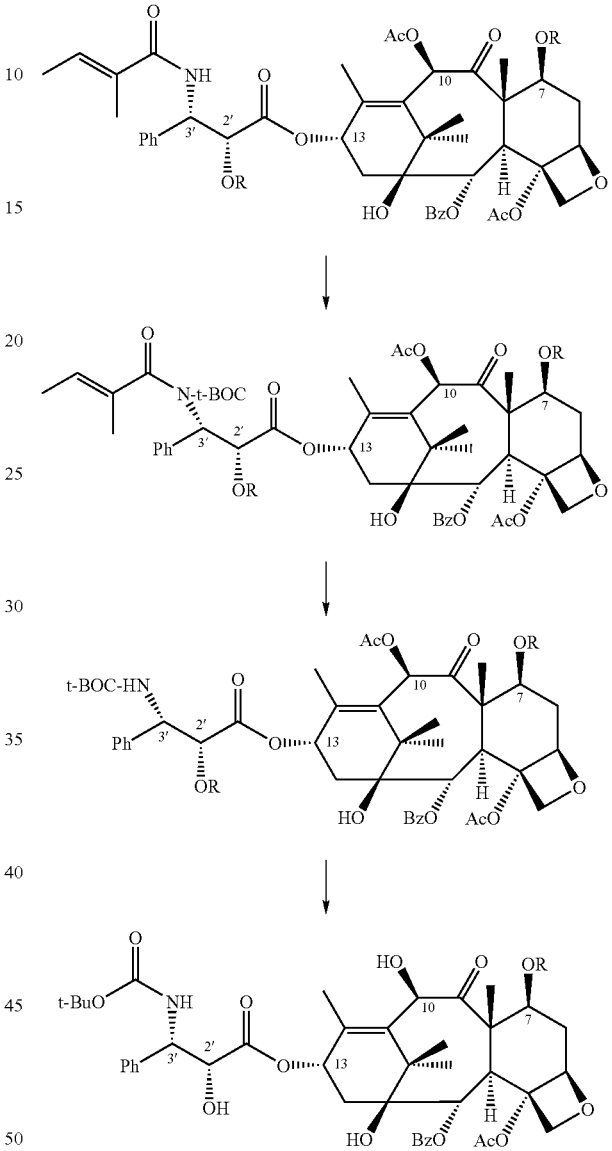

wherein R is at each occurrence independently selected from hydrogen and a hydroxyprotecting group.

* * * * *

UNITED STATES PATENT AND TRADEMARK OFFICE
CERTIFICATE OF CORRECTION

PATENT NO. : 7,585,986 B2  
APPLICATION NO. : 10/590647  
DATED : September 8, 2009  
INVENTOR(S) : Ragina Naidu Page 1 of 1

It is certified that error appears in the above-identified patent and that said Letters Patent is hereby corrected as shown below:

Column 8, line 55, delete "metbylcarbamoyloxy" and insert --methylcarbamoyloxy--.

Signed and Sealed this
Eighth Day of March, 2011

David J. Kappos
*Director of the United States Patent and Trademark Office*